United States Patent [19]

Sanders

[11] Patent Number: 5,075,080
[45] Date of Patent: Dec. 24, 1991

[54] APPARATUS FOR MEASURING THE NON-POROUS SURFACE AREA OF CARBON BLACK

[75] Inventor: Daniel R. Sanders, Nashua, N.H.

[73] Assignee: Cabot Corporation, Boston, Mass.

[21] Appl. No.: 534,405

[22] Filed: Jun. 7, 1990

Related U.S. Application Data

[60] Division of Ser. No. 423,693, Oct. 12, 1989, Pat. No. 4,970,169, which is a continuation-in-part of Ser. No. 353,928, May 19, 1989, abandoned.

[51] Int. Cl.$^5$ ............................................ G01N 15/08
[52] U.S. Cl. ........................................ 422/70; 422/62; 422/73; 422/81; 73/61 R; 73/61.1 R; 210/198.2
[58] Field of Search ................ 422/62, 70, 73, 81; 73/61 C, 61 R; 210/198.2

[56] References Cited

U.S. PATENT DOCUMENTS 4,629,566 12/1986 Prud'homme et al. ............. 110/635

OTHER PUBLICATIONS

Bagchi, R. et al., "Contamination Sources in the Cleanup of Samples for Inorganic ion Analysis", J. Chromatography, 351 (1986), 541–547.

James, L. B., "Amino Acid Analysis: a Fall-Off in Performance", J. Chromatography, 408 (1987), 291–295.

Primary Examiner—David L. Lacey
Assistant Examiner—David Redding
Attorney, Agent, or Firm—Harry J. Gwinnell

[57] ABSTRACT

An automated method for measuring the non-porous surface area of carbon black is disclosed. The method comprises passing a small sample of a CTAB-carbon black dispersion through a disposable filter to separate the carbon black with adsorbed CTAB from the filtrate containing unadsorbed CTAB. The filtrate next passes through a measuring loop and a high pressure liquid chromatography column to separate the CTAB from the other filtrate components. The CTAB is next sensed by a detector and an integrator calculates the amount of CTAB adsorbed by the carbon black and the non-porous surface area of the carbon black. The integrated apparatus for carrying out this method is also described. Once the carbon black and the CTAB are mixed, there is no further handling of the sample. The system is entirely automated and takes only a few minutes for the CTAB area determination. Measuring temperatures can also be fixed. This results in much more reproducible CTAB numbers for a particular carbon black.

3 Claims, 1 Drawing Sheet

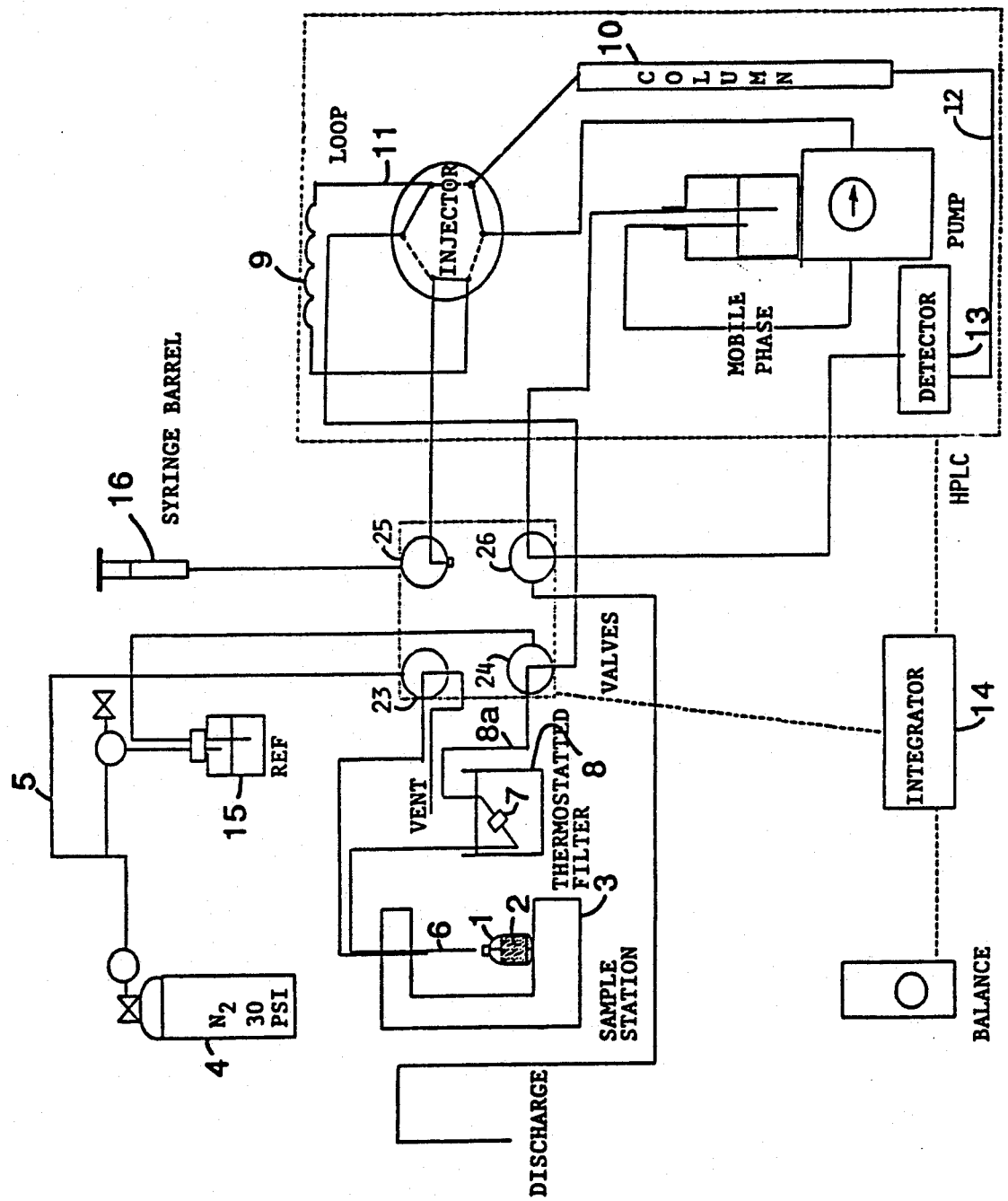

APPARATUS FOR MEASURING THE NON-POROUS SURFACE AREA OF CARBON BLACK

This application is a division of U.S. Pat. application Ser. No. 07/423,693, filed on Oct. 12, 1989, now U.S. Pat. No. 4,970,169, which is a continuation-in-part of application Ser. No. 07/353,928 filed on May 19, 1989, now abandoned.

TECHNICAL FIELD

The field of art to which this invention pertains is measuring and testing, and specifically measuring the non-porous surface are of carbon black.

BACKGROUND ART

The primary quality of a carbon black which determines its reinforcing ability is its surface area. Many methods have been developed over he years to measure the surface area. One analytical method which is used is nitrogen adsorption. In the nitrogen method the nitrogen is adsorbed onto the carbon black. The carbon black with the adsorbed nitrogen on its surface is then heated. The amount of nitrogen which is released is then measured and this amount of nitrogen is correlated to the surface area of the carbon black. One problem with the nitrogen gas test is that it measures the entire surface area. The nitrogen is adsorbed into the pores of the carbon black as well as on the gross surface. And although it is relatively fast, taking about 15 to 20 minutes, it is not useful for measuring the non-porous surface area of the carbon black. A modification of the nitrogen gas test is the nitrogen T-area analysis which uses nitrogen gas at different pressures in order to determine the surface area. However, this test takes several hours to perform.

Another analysis which has been developed to measure the surface area of carbon black is the iodine number test. This analysis is started with a definite amount of iodine, which is contacted with the carbon black. The iodine which has not been adsorbed is measured. This is a solution adsorption versus the gas adsorption used in the nitrogen method. This method is better than the nitrogen gas method in some respects because the iodine molecule which is adsorbed is a relatively large molecule and doesn't get into the pores (other than some of the medium sized pores). The iodine also has the advantage of being readily adsorbed by the carbon black. The method is also relatively easy to perform by simply dissolving the iodine in water and mixing it with the carbon black. The mixture is centrifuged, and the supernatant is separated and the amount of iodine measured by titration. There is a disadvantage with the iodine analysis, however, in that the iodine number is influenced by factors not related to surface area. If the carbon black has solvent-extractable impurities, these will affect the numbers. For example, the iodine number of a fluffy black versus pellets will be different, even though the carbon black used has the same non-porous surface area. If the black is oxidized, this will also affect how much iodine is adsorbed. The analysis is capable of being deceived by non-surface area factors. Therefore it is possible to get blacks with the same iodine number, but not the same non-porous surface area, or 2 blacks with different iodine numbers can actually have the same non-porous surface area, because of surface impurities.

An additional analysis which overcomes some of the disadvantages of the above methods is commonly referred to as the CTAB analysis. This analysis involves the use of a large organic molecule, cetyltrimethylammonium bromide (i.e. CTAB). This analysis is similar to the iodine number analysis in that the CTAB is adsorbed onto the surface of the carbon black. However, it is immune to non-surface area factors. On the other hand, it is a more time consuming method than the iodine number method and is subject to more inaccuracies for other reasons. Like the iodine number method this is a solution method where the CTAB is dissolved in water. The carbon black is placed in a bottle with a stirrer, the CTAB is added, and the mixture stirred to make a dispersion. The dispersion is then filtered and the filtrate collected. The amount of CTAB in the filtrate is then measured and based on this amount, the amount of CTAB adsorbed by the carbon black and the non-porous surface area of the carbon black are determined. Because of the amount of material handling which is required by this method, results of the CTAB analysis can often be erratic. The method is also very time consuming, with generally only about 4 samples per hour capable of being processed. While the CTAB analysis is better in some respects than the iodine number analysis, it is also more time consuming and prone to unreliability.

Accordingly, what is needed in this art is an improved analysis method for determining the non-porous surface area of carbon black which overcomes the above problems.

BRIEF SUMMARY OF INVENTION

The present invention is directed to an automated method for measuring the non-porous surface area of a porous carbon black. The method comprises dispersing a sample of carbon black in a solution of cetyltrimethylammonium bromide where part of the CTAB is adsorbed by the carbon black. The dispersion is made in a closed container and for all of the subsequent processing is not handled manually. A small amount of the dispersion is forced from the sample container through a filter. The filtrate is then passed through a measuring loop which measures a predetermined volume of the filtrate. The predetermined volume of filtrate is then injected onto a high pressure liquid chromatography column (HPLC) which separates CTAB from the other solution components, which CTAB is then measured. This measurement is used to calculate the amount of CTAB adsorbed by the carbon (and thus the non-porous surface area of the carbon).

A closed system for automatically determining the non-porous surface area of a porous carbon black is also described. This system comprises a container for containing a CTAB-carbon black dispersion, a means for forcing the dispersion out of the container, a temperature controlled filter for filtering the dispersion, a measuring loop for measuring a specified amount of the filtrate, and a high pressure liquid chromatography column for separating CTAB from other filtered components. The system also includes a detector for measuring the amount of CTAB separated and an integrator for determining the amount of CTAB adsorbed by the carbon. The system is a closed system requiring virtually no handling of solutions during processing.

The automatically operated method and apparatus results in reduced handling of the materials involved, improved reproducibility of results for particular carbon blacks, reduced time for sample measurement, and increased precision of measurement.

BRIEF DESCRIPTION OF THE DRAWING

The FIGURE shows an apparatus for automatically measuring the CTAB surface area of a carbon black.

DETAILED DESCRIPTION OF THE INVENTION

In the FIGURE, the container (1) is typically made of a glass which can take the high pressures produced by the gas used to force the dispersion out the container. The container contains a dispersion (2) of carbon black and CTAB. The container sits on a holder (3) which holds the container immobile. In operation, gas (preferably nitrogen) is forced into the container from a gas source (4) through a gas line (5) into the container forcing the dispersion out of a flow line (6) through a disposable filter-containing cartridge (7). The filter is contained in a means (8) for thermostatically controlling the temperature of the filter at all times. The CTAB solution, with the filtered carbon black left behind, then passes through a flow line (8a) into a measuring loop 9). This loop is typically stainless steel and measures a predetermined amount of the filtrate. While this measuring means is described as a loop, any comparable in-line measuring means can of course be used such as a tube, bulb, etc. This predetermined amount of filtrate is then injected onto a high pressure liquid chromatography column (10) through a fluid line (11). This separates the CTAB from other components of the filtrate. The separated CTAB is then passed through a flow line (12) into a detector 13). A standard chromatographic curve is generated by the detector and the area under the curve measured by the integrator (14). The integrator computes the CTAB area for the particular carbon black from this area.

EXAMPLE 10.974 grams ($\pm 0.002$ g) of CTAB were weighed into a 400 milliliter tared beaker. A 1.5 inch stir bar was carefully added. About 300 milliliters from exactly 1 liter of nanopure water was added from a 1 liter silanized volumetric flask. The beaker was covered with a watch glass and the CTAB was dissolved using low heat and slow stirring by using a hot plate/stirrer. At 35° C. dissolution was complete in about 15 minutes). The solution was quantitatively transferred to a 4 liter amber reagent bottle containing exactly 2 liters of nanopure water (from a silanized volumetric flask) using the remainder of the 1 liter for the transfer. The solution was briefly stirred or swirled to obtain uniformity. CTAB was brought to 23.5° C. before using (digital thermometer) either by placing the bottle in a 23.5° C. jacketed container overnight or a cold bath for a few minutes while monitoring the temperature. The Kg jar of CTAB was stored in a desicator. A 5 millimolar (mM) reference solution was prepared (15 in the FIGURE) gravimetrically by combining exactly ($\pm 0.01$ g) equal weights (approximately 350 g each) of nanopure water and 10 millimolar CTAB in a 1 liter Erlenmeyer flask using a 1200 gram capacity top loading balance. The solution was swirled and transferred to a 2 liter reservoir. Another approximately 700 milliliters was prepared the same way and added to the 2 liter reservoir. The reservoir was capped and pressurized to 30 psi. The valve was switched off to isolate the air in the reservoir from the pressure system.

Solutions of about 2,3,4,6,7, and 8 millimoles were prepared gravimetrically by combining the appropriate weights of 10 millimolar CTAB and nanopure water in 140 milliliter bottles on a top-loading balance. Quantities were weighed to the nearest 0.01 g.

59.5 g reagent KBr was dissolved in approximately 300 milliliter nanopure water from a 1 liter graduated cylinder. The solution was vacuum filtered through a 0.2 micron Nylon TM 66 membrane filter and combined with the remaining $H_2O$ (total volume 1018 milliliter).

Nylon TM 66 is a manufactured fiber in which fiber-forming substances are any long chain synthetic polyamide having recurring polyamide groups as an integral part of the polymer chain.

300 milliliter nanopure water ($\pm 2$ milliliter )+100 milliliter ($\pm 0.5$ milliliter ) of the above KBr reagent solution were swirled together in a 1 or 2 liter polyethylene bottle. 600 milliliter acetonitrile (ACN) ($\pm 3$ milliliter ) was added. The solution was swirled and vacuum filtered through a 0.2 micron Nylon TM 66 filter. This also served to degas the solution. A 50 milliliter Universal Repipet dispenser was attached to a reagent bottle containing 22°-25° distilled water. Water was dispensed by raising the plunger slowly to avoid "spitting", and then allowing the plunger to descend by gravity. Bubbles were carefully excluded from the system. The water dispensed during the descent was collected in a tared vessel and the pipet stop adjusted until the weight was 29.922$\pm$0.02. gram. The precision was checked by taking 18 consecutive aliquots of 30.01 milliliter (29.933 gram) and weighing each to the nearest 0.001 gram. The results showed, a precision of 0.007 gram (1 sigma), that is a 95% confidence variability (2 sigma) of 0.05%. At the end of a series of analyses (e.g., end of day) the dispenser was removed from the CTAB, and carefully flushed with distilled water. The dispenser was inverted in a gallon tub of distilled water 22° to 35° C.) and gently cycled a few times to remove accumulated CTAB. Care was taken to avoid disturbing the calibration stop. When a new series of analyses was to be run (e.g. next morning) the pipet was attached to the CTAB bottle (in its thermostated bath) and flushed with distilled water three times with 30 milliliter amounts. The last 30 milliliters was collected in a tared bottle to check the calibration. The CTAB solution layer between the barrel and the plunger tended to precipitate causing possible erroneous dosing and/or sticking pipet action. The temperature of the solution in the dispenser below the plunger was not controllable. Because of these consideration, 30 milliliters of solution was discarded immediately before each sample was dosed. Care was taken to insure that dosing was done as in the precision study. Bubbles that occasionally formed in the pipet were expelled. Samples, batch-weighed, were dosed one at a time, crimp-capped with a silicone rubber septum and analyzed immediately.

Blacks were analyzed in random orders on each day. It was not necessary to dry the carbon black samples, rather non-dried samples were analyzed and their moisture content measured and the measured CTAB areas corrected for moisture content. The identification of the black and its moisture content were entered into the integrator. The blacks were weighed into the sample bottles and the weights electronically transmitted to the integrator. Stir bars were also added to the sample bottles. The capped 30 milliliter hypovial sample bottle with carbon black, stir bar and CTAB was placed in a tripod shaped cradle which fit onto a submersible stirrer which was located on the bottom of a Bransonic B2200 Ultrasonic Cleaner 100 watt). This tripod allowed a ⅜ inch space between the bottle bottom and the stirrer to allow ultrasonically active water to surround the bottle. The cradle also stabilized the bottle at high spin speeds. The stirrer was set at approximately half speed corresponding to the maximum stir speed that would produce a stable vortex. When the vortex stability was visually confirmed (approximately 5 seconds), the ultrasonication period of 3 minutes was initiated, and a 5.5 minute timer was started. A 2.5 minute post-ultrasonic stirring period was incorporated to assure equilibration after dispersing. During the dispersing period of the first sample of a series, approximately 4 milliliter reference CTAB was forced into the mounted syringe (16) (with plunger) by turning off valve 25 and turning on valve 24. Valve 24 was then turned off, and with the filtrate and dispersion lines joined, the CTAB was syringe-pumped through the loop and flow lines to expel any water left from the end of the previous set of analyses. Valve 25 was turned on. The dispersion line was separated from the filtrate line, and elevated to allow CTAB to drain out the needle into a waste bottle (not shown). The needle was blotted with a tissue.

Filters were not pre-treated with CTAB, but used as is, dry. A 0.1 micron Duropore ™ Filter (a polyvinylidene difluoride membrane filter, Millipore Corp.) was attached to the filtrate line, then the dispersion line, and immersed in the 23.5° C. temperature control means, diagonally, outlet side up. The filter was temperature-equilibrated at least 1 minute before analysis was initiated. Immediately after the 5.5 minute dispersion period, the bottle (1) was placed in the sample station (3) and the analysis started by pressing an "Inject" button on the integrator (14). This led to the following sequence of events. The needles moved into the bottle and pressurized it to 30 psi with $N_2$. The loop was flushed with 1 milliliter reference CTAB, exactly 50 microliters of which was injected onto the HPLC column.

Filtration was initiated at 0.31 minute by opening valves 24 and 25. This allowed filtrate to flow around the loop (still in the inject position) to the plungerless syringe. This initial surge expelled most of the air from the filter, and avoided trapping bubbles in the loop. The orientation of the filter (not vertical) also helped trap bubbles in the uppermost section of the filter cartridge (See the FIGURE). At 0.82 minute the loop was returned to load position to allow approximately half the filtrate (approximately 1 to 1.5 milliliters) to flush the loop. At 1.3 minutes valve 26 was changed from re-circulate mode to discharge mode to prevent accumulation of CTAB solution in the mobile phase. During each run 11.4 milliliters of mobile phase was discharged to drain and flushed with a large excess of water.

At 3.3 minutes the loop was pressurized by closing valve 25. This minimized the volume error due to any bubbles trapped in the loop. At 3.5 minutes, just after elution of the reference peak, the filtrate was injected into the column. (The reference CTAB was similarly pressurized between 0.12 and 0.3 minute). The total volume (reference plus filtrate) collected in the syringe was recorded and the filtrate discarded. At 3.55 minutes the sample bottle was vented and the needles were automatically withdrawn from the sample bottle. A waste bottle was placed under the needles, the filter discarded, and the dispersion line raised to drain it.

The sample bottle was removed, decapped and emptied through a basket in the sink to retrieve the stir bar. The bottle was rinsed twice with warm water and examined for evidence of incomplete dispersion (an extremely rare event) such as black stuck to the side. The bottle was immersed in a gallon tub of mildly soapy warm water. The needle was blotted with a tissue and a new filter installed as previously described. At this point there were about 2 minutes left before the near-simultaneous conclusion of the analysis of this sample and the dispersing of the next. Immediately after initiating the sequence of events described above by pressing the "Inject" button on the integrator, the analyst started the next sample by adding CTAB and dispersing, as described previously for the first sample. The timing was such that this sample was ready to place in the sample station just as the integrator was reporting the results for the previous sample. While the length of the cycle per sample was 14 minutes, there was an overlap of 7 minutes for a net time consumption of 7 minutes and thus 8 samples were run in 63 minutes. After the last sample, valve 25 was opened and the filtrate line was joined to the dispersion line and a syringe full of nanopure water was forced through the loop, lines and needle to waste. Avoiding introduction of air, valve 25 was shut to prevent siphoning. The high pressure liquid chromatograph was left on continuously.

While carbon blacks of any surface area per gram can be analyzed by the present invention, the particular system of the present invention is specifically designed to measure carbon black samples having 30 to 70 square meters of total surface area, with a target of 50 $m^2$ surface area per sample. With carbon black samples of this surface area, each sample bottle is designed to contain exactly 30 milliliters of 10 millimolar concentration CTAB (0.3 millimole per sample).

The CTAB and carbon black are dispersed for approximately 3 minutes (typically followed by a 2.5 minute post-sonification stir) This takes place typically at a temperature of 23.5° C., although temperatures in the range of about 22° C. to 25° C. can be used, as long as the temperature at which the samples are analyzed is the same as the temperature used for calibration. The gas used to pressurize the system was nitrogen gas. The pressure used to pressurize the system and force the solution out of the sample bottle is 30 psi (±2 psi).

The filter-cartridge used was a single unit, disposable, plastic Millex Duropore filter-cartridge. The filter material in the unit was a 0.1 micron porosity Duropore PVDF (polyvinylidene diflouride). The tubing used was Teflon ™ (tetrafluoroethylene) tubing 1/16 inch outer diameter and 0.5 millimeter inner diameter. The measuring loop is made out of stainless steel and preferably 316 stainless steel. The volume of material measured and sent into the HPLC is 25 microliters to 75 microliters, and preferably 50 microliters.

The HPLC column is a strong cation exchange type column (Alltech SCX), i.e. sulfonate groups bonded to (5 micron diameter) silica particles. The detector used to measure the CTAB is a differential refractometer. The area under the generated peak is integrated to generate the CTAB area ($m^2$/gram).

The temperature of the filter is controlled by immersing the filter in a temperature controlling means comprising a Dewar flask which contains water and a coil of copper tubing through which water at 23.5° C. is pumped.

The initial 10 millimolar CTAB solution, ultrasonic bath, and filter were maintained at 23.5° C. (±0.2° C.) by a refrigerator bath circulator assisted by a suction pump. The HPLC consisted of a Spectra Physics 8100 pump with column-over (set for 30° C.). In the example the mobile phase is 60% acetonitrile in water, 50 mM KBr. The pump flow was 2 milliliter/minute, pressure approximately 2200 psi. The injection valve in the instrument was a Valco 6CW valve. The detector was Knauer Model 198 Differential Refractometer. The valves were pneumatically activated (60 psi filtered air) 3-way Teflon TM slider valves made by Altex or Rheodyne. They were controlled by solenoids from Rheodyne, and interfaced to the integrator by means of a solenoid interface from Rainin.

The non-porous surface area of the carbon black responsible for the cetyltrimethylammonium bromide adsorption is determined according to the following formula, $$\frac{K' - K'' \times R}{W((100 - M)/100)}$$

where $K'$ and $K''$ are calibration constants, R is the ratio of chromatographic filtrate peak area to chromatographic reference peak area, W is the weight of the carbon black sample, and M is the percent moisture in the carbon black sample.

The constants $K'$ (intercept) and $K''$ (slope) are linear regression constants generated from a six point calibration curve obtained by running in the present system the appropriate weights of ASTM Reference Black IRB#3 (surface area 83 meters per gram) encompassing surface areas of 30 to 70 meters squared. In fact, one of the advantages of the system according to the present invention is that it does not need recalibration when a new CTAB solution (or reference solution) is prepared so long as the solution is prepared from the same lot of CTAB powder. This allows an analyst to test about 4500 samples before recalibration (assuming a 1.0 kilogram lot/jar of CTAB powder).

The integrator was a Spectra Physics 4270 with BASIC programing, serial interface, and external events module (with cable). A sample CTAB area was calculated by the integrator according to the above equation where $K'$ and $K''$ were determined by the method specified above to be 95.37 and 48.63 respectively. The sampling station was adapted from a multisampler, operated in one-sample mode. The 18 gauge needles were mounted in an aluminum block which could be raised or lowered by a pneumatic linear cylinder from Techno, which was controlled by the same solenoid that activated valve 23 (the pressure/vent valve). The liquid lines were all 0.5 millimeter inner diameter Teflon TM lines (1/16 inch outer diameter) joined by flanged connectors. The connections to the filter were by means of Luer adaptors. The pneumatic lines were either ¼ inch outer diameter polyvinyl chloride or ⅛ inch outer diameter Teflon TM lines.

The 5 millimolar reservoir was a 2 liter plastic coated HPLC solvent reservoir with conical bottom obtained from Rainin, with a three-holed Teflon TM cap from Kontes. The filter thermostat was a 500 milliliter Dewar in which was immersed a coil of ¼ inch copper tubing through which 23.5° C. water circulated. The re-circulating filter was a Gelman 0.2 micron Teflon TM cartridge (1 inch diameter). The sample bottles ("hypovials") was 30 milliliter glass bottles from Pierce.

The 50 milliliter Repipet was from Lab Industries. The submersible stirrer and external controller were from Whatman Lab Sales.

As can be seen from the above, the CTAB solution is accurately prepared and protected from precipitation by the use of constant temperatures, the dispensing of the CTAB is done in a highly precise manner, dispersion techniques have been improved, small volumes and disposable cartridge filters are used, and the filtrate is analyzed without manual handling. The temperature of adsorption and filtration are also fixed. All of these contribute to the improved accuracy and reproducibility of the present system and method.

As stated above customers purchasing carbon black have come to rely on specific CTAB numbers for placing their blacks into their products. In order for predictability of performance it is important that these numbers be as accurate as possible. Conventional CTAB testing up to this point has not had the reliability desired for these purposes. Part of this problem has been the result of the large amount of handling necessary for doing conventional CTAB testing. With the CTAB testing of the present invention, the handling problems which have previously existed have been eliminated. Also, smaller volumes are involved in the measuring, and faster times. In addition, temperature control is used at critical locations further increasing the accuracy of the CTAB measurement.

I claim:

1. A closed system for automatically, quickly and precisely determining the amount of cetyltrimethylammonium bromide adsorbed by the carbon black in a cetyltrimethylammonium bromide-carbon black dispersion comprising, a container for holding a dispersion of cetyltrimethylammonium bromide and carbon black, a means for forcing the dispersion out of the container, a filter having thermostatic temperature control means in fluid flow communication with the container for filtering the carbon black with adsorbed cetyltrimethylammonium bromide from the dispersion to form a filtrate, a measuring loop in fluid flow communication with the filter for measuring a specified amount of the filtrate, a high pressure liquid chromatography column in fluid flow communication with the measuring loop for separating cetyltrimethylammonium bromide from the remainder of the filtrate, detector means for quantitatively sensing the presence of cetyltrimethylammonium bromide separated, and integrator means for determining the amount of cetyltrimethylammonium bromide sensed by the detector means and relating that amount to the amount of cetyltrimethylammonium bromide adsorbed by the carbon black.

2. The system of claim 1 wherein the means for forcing the dispersion out of the container is a pressure source in fluid flow communication with the container.

3. The system of claim 1 wherein the filter is disposable.

* * * * *